US007195891B2

(12) United States Patent
Yuan et al.

(10) Patent No.: US 7,195,891 B2
(45) Date of Patent: Mar. 27, 2007

(54) METHODS AND COMPOSITIONS OF ENZYMATIC CYCLING BASED ASSAYS FOR MYELOPEROXIDASE

(75) Inventors: Chong-Sheng Yuan, San Diego, CA (US); Chao Dou, San Diego, CA (US)

(73) Assignee: General Atomics, San Diego, CA (US)

( * ) Notice: Subject to any disclaimer, the term of this patent is extended or adjusted under 35 U.S.C. 154(b) by 0 days.

(21) Appl. No.: 10/916,563

(22) Filed: Aug. 11, 2004

(65) Prior Publication Data

US 2006/0035308 A1 Feb. 16, 2006

(51) Int. Cl.
*C12Q 1/28* (2006.01)

(52) U.S. Cl. ........................................................ 435/28

(58) Field of Classification Search ..................... 435/4
See application file for complete search history.

(56) References Cited

U.S. PATENT DOCUMENTS

| | | | | |
|---|---|---|---|---|
| 6,022,699 | A | 2/2000 | Graff et al. | 435/28 |
| 2002/0164662 | A1 | 11/2002 | Hazen et al. | 435/7.21 |
| 2003/0060490 | A1 * | 3/2003 | Voziyan et al. | 514/351 |

FOREIGN PATENT DOCUMENTS

WO WO 02/090575 11/2002

OTHER PUBLICATIONS

Anderson, M. M. et al, "Human Neutrophils Employ the Myeloperoxidase-Hydrogen Peroxide-Chloride System to Convert Hydroxy-amino Acids into GLycoladehyde, 2-Hydroxpropanal, and Acrolein", Feb. 1997, J. Clin. Invest., vol. 99, No. 3, pp. 424-432.*

Al-Maghrebi, M. A. et al, "Glycolaldehyde induces apoptosis in a human breast cancer cell line", online Jul. 17, 2003, Archives of Biochemistry and Biophysics, vol. 417, pp. 123-127.*

Holmes, R. P. et al, "Glyoxylate Synthesis, And Its Modulation And Influence on Oxalate Synthesis", Nov. 1998, J. of Urology, vol. 160, No. 5, pp. 1617-1624.*

Kishi, K. et al, "Highly Sensitive Cholesterol Assay with Enzymatic Cycling Applied to Measurement of Remnant Lipoprotein-Cholesterol in Serum", May 2002, Clinical Chemistry, vol. 48, No. 5, pp. 737-741.*

Van Schaftingen, E. et al, "Coenzyme specificity of mammalian liver D-glycerate dehydrogenase", Dec. 8, 1989, Eur. J. Biochem., vol. 186, pp. 355-359.*

Barone et al., J. Neuroscie. Res. (1991) 29:336-345.

Bennett et al., Br. J. Haematol. (1976) 33:451-458.

Brennan et al., N. Engl. J. Med. (2003) 349:1595-1604.

Cascorbi et al., Cancer Res. (2000) 60:644-649.

Dautherty et al., J. Clin. Invest. (1994) 94:437-444.

Hazell et al., J. Clin. Invest. (1996) 97:1535-1544.

Heinecke et al., Curr. Opinion Lip. (1997) 8:268-274.

Hoy et al., Clin. Chem. Lab. Med. (2002) 40:2-8.

Jolivalt et al., Neurosci. Lett. (1996) 210:61-64.

Le Marchand et al., Cancer Epidermiol. Biomarkers Prev. (2000) 9:181-184.

London et al., Cancer Res. (1997) 57:5001-5003.

Malle et al., Eur. J. Biochem. (2000) 267:4495-4503.

Marquez et al., J. Biol. Chem. (1990) 265:5666-5670.

Misra et al., Cancer Lett. (2001) 164:161-167.

Nagra et al., J. Neuroimmunol. (1997) 78:97-107.

Re et al., Eur. J. Emerg. Med. (1997) 4:5-9.

Reynolds et al., Blood (1997) 90:2730-2737.

Schabath et al., Carcinogenesis (2000) 21:1163-1166.

Anderson et al., Journal of Clinical Investigation (1997) 99(3):424-432.

Boronat et al., Journal of Bacteriology (1983) 153(1):134-139.

International Search Report for PCT/US2005/028540, mailed on Jan. 5, 2006, 5 pages.

Kettle et al., Biochemical Pharmacology (1991) 41(10):1485-1492.

* cited by examiner

*Primary Examiner*—Christopher R. Tate
*Assistant Examiner*—Amanda P. Wood
(74) *Attorney, Agent, or Firm*—Morrison & Foerster LLP

(57) ABSTRACT

The present invention provides a method for assaying myeloperoxidase activity. In the assay, a sample containing myeloperoxidase or suspected of containing myeloperoxidase is contacted with substrate including serine, hydrogen peroxide, and a halide. If myeloperoxidase is present in the sample, serine is converted into glycolaldehyde, which is further converted into glycolate by a glycoaldehyde converting enzyme. The method then utilizes a cycling reaction system between glycolate and glyoxylate to generate a detectable signal that corresponds to the myeloperoxidase activity. Kits for assaying myeloperoxidases based on the same principle are also provided.

21 Claims, No Drawings

METHODS AND COMPOSITIONS OF ENZYMATIC CYCLING BASED ASSAYS FOR MYELOPEROXIDASE

CROSS-REFERENCE TO RELATED APPLICATIONS

Not applicable.

STATEMENT REGARDING FEDERALLY SPONSORED RESEARCH OR DEVELOPMENT

Not applicable.

FIELD OF THE INVENTION

This invention relates generally to the field of myeloperoxidase detection. In particular, the invention provides methods and kits for assaying myeloperoxidase in samples.

BACKGROUND OF THE INVENTION

Myeloperoxidase (MPO; EC 1.11.1.7) is a tetrameric, heavily glycosylated basic heme protein of approximately 150 kDa. It is composed of two identical disulfide-linked protomers, each of which possesses a protoporphyrin-containing 59–64 kDa heavy subunit and a 14 kDa light subunit. U.S. Pub. No. 2002/0164662; Hoy et al., *Clin. Chem. Lab. Med.* 40: 2–8 (2002). In vivo, MPO converts $Cl^-$ via a two-electron peroxidation step into hypochlorous acid, HOCl, a powerful oxidizing agent capable of destroying microbes. Marquez et al., *J. Biol. Chem.* 265: 5666–5670 (1990).

MPO plays an important role in host defense against invading microorganisms. MPO is abundant in neutrophils and monocytes, accounting for 5% and 1 to 2% of the dry weight of these cells respectively. Marquez et al., *J. Biol. Chem.* 265: 5666–5670 (1990); U.S. Pub. No. 2002/0164662.

MPO is implicated in a large spectrum of diseases. Besides participating in the defense against microorganisms via the production of HOCl, MPO is released in inflammatory states where migrating neutrophils may release active enzyme. Hoy et al., *Clin. Chem. Lab. Med.* 40: 2–8 (2002). Increased MPO levels have been reported in infections and anti-MPO antibodies accumulate in systemic vasculitites. MPO is also involved in non-infectious diseases, such as atherosclerosis, cancer and promyelocytic leukemia, neurodegerative diseases including Alzheimer's disease and multiple sclerosis. Hoy et al., *Clin. Chem. Lab. Med.* 40: 2–8 (2002).

MPO mRNA is widely used in clinical chemistry as a marker for acute myeloid leukemia (AML). Bennett et al., Br. *J. Haematol.* 33: 451–8 (1976). Higher expression genotype of the MPO G-463A polymorphism has also been reported to be related to AML. Reynolds et al., *Blood* 90: 2730–7 (1997). The MPO G-463A polymorphism characterized by a G/A transition is located with Alu sequences of a promoter region containing a hormone response element. The G/G genotype has been related to increased MPO expression and protein level in cells of leukemic patients. Reynolds et al., *Blood* 90: 2730–7 (1997). It has also been shown that subjects homozygous for the A allele are at a decreased risk for lung cancer. London et al., *Cancer Res.* 57: 5001–3 (1997); Le Marchand et al., *Cancer Epidermiol. Biomarkers Prev.* 9: 181–4 (2000); Cascorb et al., *Cancer Res.* 60: 644–9 (2000); Schabath et al., *Carcinogenesis* 21: 1163–6 (2000). However, a recent study shows that the A allele is associated with an increased risk of lung cancer among a subset of older men. Misra et al., Cancer Lett. 164: 161–7 (2001).

MPO is present in the microglia in the brain of patients with multiple sclerosis (MS) and in the microglial cells surrounding senile plaques of cerebral cortex from Alzheimer's disease (AD) cases. Jolivalt et al., *Neurosci. Lett.* 210: 61–4 (1996); Nagra et al., *J. Neuroimmunol.* 78: 97–107 (1997). An alternation of MPO level is also related to atherosclerosis and brain infarction. It has been reported that $MPO/H_2O_2/Cl^-$ system is one of the possible mechanisms involved in the initiation of atherosclerotic lesions. Dautherty et al., *J. Clin. Invest.* 94: 437–44 (1994). Heinecke et al. *Curr. Opinion Lip.* 8: 268–74 (1997); Hazell et al., *J. Clin. Invest.* 97: 1535–44 (1996); Malle et al., *Eur. J. Biochem.* 267: 4495–503 (2000). One of the main consequences of atherosclerosis is brain infarction and measurement of MPO activity is a widely used marker of neutrophil infiltration of the brain parenchyma. Barone et al., *J. Neuroscie. Res.* 29: 336–45 (1991). Increased MPO activity has been observed in the serum of patients after an ischemic brain infarct. Re et al., *Eur. J. Emerg. Med.* 4: 5–9 (1997). Measurement of MPO has also been used for predicting cardiovascular risks. Brennan et al., *N. Engl. J. Med.* 349: 1595–1601 (2003); U.S. Pub. No. 2002/0164662.

The broad range of diseases MPO is implicated in, and the possibility of using MPO as a clinical marker and therapeutic target, make assays for accurately measuring MPO levels and activities invaluable. Several assay methods have been reported. WO 02/090575, U.S. Pat. No. 6,022,699. However, there is still a need for a reliable and sensitive method for assaying MPO.

BRIEF SUMMARY OF THE INVENTION

The invention provides methods for assaying a myeloperoxidase in a sample, said method comprises: a) contacting a sample suspected of containing a myeloperoxidase with serine, hydrogen peroxide, and chlorine to generate glycolaldehyde; b) converting said glycolaldehyde generated in step a) to glycolate in the presence of a glycolaldehyde converting enzyme and a first electron acceptor in its oxidized form; c) converting said glycolate from step b) to glyoxylate in the presence of a second electron acceptor in its oxidized form and a glycolate converting enzyme, whereby reduced form of the second electron acceptor is generated; said glyoxylate is converted back to glycolate in the presence of a third electron acceptor in its reduced form and a glyoxylate converting enzyme to form a cycling reaction system, whereby oxidized form of the third electron acceptor is generated; wherein the second electron acceptor and the third electron acceptor are different; and d) assessing concentration change of the reduced or oxidized form of the second electron acceptor or the reduced or oxidized form of the third electron acceptor in said cycling reaction system, whereby the presence, absence and/or the amount of the myeloperoxidase in the sample is determined.

In some embodiments, the first electron acceptor in step b) is different from the second electron acceptor and/or the third electron acceptor in step c). In other embodiments, the first electron acceptor in step b) and the second electron acceptor in step c) are the same. In still other embodiments, the first electron acceptor in step b) and the third electron acceptor in step c) are the same.

In some embodiments, the sample suspected of containing a myeloperoxidase is contacted with serine, hydrogen peroxide, chlorine, the glycolaldehyde converting enzyme, and the first electron acceptor in its oxidized form. In other embodiments, the sample suspected of containing a myeloperoxidase is contacted with serine, hydrogen peroxide, chlorine, the glycolaldehyde converting enzyme, the first electron acceptor in its oxidized form, the glycolate converting enzyme, and the second electron acceptor in its oxidized form.

In some embodiments, the glycolaldehyde converting enzyme of step b) is a glycolaldehyde dehydrogenase, and the first electron acceptor is selected from the group consisting of $NAD^+$, $NADP^+$, thio-$NAD^+$, thio-$NADP^+$, acetyl-$NAD^+$, and acetyl-$NADP^+$.

In some embodiments, the glycolate converting enzyme and the glyoxylate converting enzyme in the cycling reaction system of step c) are different. In some embodiments, the glycolate converting enzyme does not react with the third electron acceptor or has lower affinity for the third electron acceptor than the second electron acceptor, and the glyoxylate converting enzyme does not react with the second electron acceptor or has lower affinity for the second electron acceptor than the third electron acceptor. In some embodiments, the glycolate converting enzyme is a glycolate reductase or a glycolate oxidase. In some embodiments, the glyoxylate converting enzyme is a glyoxylate reductase or a D-glycerate dehydrogenase.

In some embodiments, the glycolate converting enzyme is a glycolate reductase, and the glyoxylate converting enzyme is a glyoxylate reductase. For these embodiments, the oxidized form of the second electron acceptor may be selected from the group consisting of $NAD^+$, $NADP^+$, thio-$NAD^+$, thio-$NADP^+$, acetyl-$NAD^+$, and acetyl-$NADP^+$, and the reduced form of the third electron acceptor may be selected from the group consisting of NADH, NADPH, thio-NADH, thio-NADPH, acetyl-NADH, acetyl-NADPH, (R)-lactate, 2,6-dichloroindophenol, and phenazine methosulfate.

In other embodiments, the glycolate converting enzyme is a glycolate oxidase, and the glyoxylate converting enzyme is a D-glycerate dehydrogenase. For these embodiments, the oxidized form of the second electron acceptor may be $O_2$, and the reduced form of the third electron acceptor may be selected from the group consisting of NADH, NADPH, thio-NADH, thio-NADPH, acetyl-NADH, acetyl-NADPH.

In some embodiments, the glycolate converting enzyme and the glyoxylate converting enzyme in the cycling reaction system of step c) are the same. For example, both the glycolate converting enzyme and the glyoxylate converting enzyme are a glycolate reductase or a glyoxylate reductase. The oxidized form of the second electron acceptor may be selected from the group consisting of $NAD^+$, $NADP^+$, thio-$NAD^+$, thio-$NADP^+$, acetyl-$NAD^+$, and acetyl-$NADP^+$, and the reduced form of the third electron acceptor is selected from a group consisting of NADH, NADPH, thio-NADH, thio-NADPH, acetyl-NADH, and acetyl-NADPH.

The concentration change of the reduced or oxidized form of the second electron acceptor or the reduced or oxidized form of the third electron acceptor in said cycling reaction system may be assessed by photometric method.

The methods of the invention may further comprise a step of coupling the oxidized or reduced form of the second electron acceptor or the reduced or oxidized form of the third electron acceptor to a color-producing agent after step d), wherein the concentration change of the oxidized or reduced form of the second electron acceptor or the reduced or oxidized form of the third electron acceptor is assessed by a colorimetric method.

The sample that may be assayed by the methods of the invention includes a biological fluid. The biological fluid may be blood, serum, plasma or urine.

The methods of the invention may be used for prognosis and/or diagnosis of a disease. Examples of such disease are atherosclerosis, stroke, multiple sclerosis, Alzheimer's disease, lung cancer, leukemia, and infection.

The invention also provides kits for assaying myeloperoxidase, comprising: serine, hydrogen peroxide, chlorine, a glycolaldehyde converting enzyme which catalyzes conversion of glycolaldehyde to glycolate and a first electron acceptor in its oxidized form, a glycolate converting enzyme which catalyzes conversion of glycolate to glyoxylate and a second electron acceptor in its oxidized form, and a glyoxylate converting enzyme which catalyzes conversion of glyoxylate to glycolate and a third electron acceptor in its reduced form, wherein the second electron acceptor and the third electron acceptor are different.

In some embodiments, the first electron acceptor in step b) is different from the second electron acceptor and/or the third electron acceptor in step c). In other embodiments, the first electron acceptor in step b) and the second electron acceptor in step c) are the same. In still other embodiments, the first electron acceptor in step b) and the third electron acceptor in step c) are the same.

In some embodiments, the glycolaldehyde converting enzyme is a glycolaldehyde dehydrogenase and the first electron acceptor is selected from the group consisting of $NAD^+$, $NADP^+$, thio-$NAD^+$, thio-$NADP^+$, acetyl-$NAD^+$, and acetyl-$NADP^+$.

In some embodiments, the glycolate converting enzyme and the glyoxylate converting enzyme in the cycling reaction system of step c) are different. In some embodiments, the glycolate converting enzyme is a glycolate reductase and the oxidized form of the second electron acceptor is selected from the group consisting of $NAD^+$, $NADP^+$, thio-$NAD^+$, thio-$NADP^+$, acetyl-$NAD^+$, and acetyl-$NADP^+$; and the glyoxylate converting enzyme is a glyoxylate reductase and the reduced form of the third electron acceptor is selected from the group consisting of NADH, NADPH, thio-NADH, thio-NADPH, acetyl-NADH, and acetyl-NADPH (R)-lactate, 2,6-dichloroindophenol, and phenazine methosulfate.

In other embodiments, the glycolate converting enzyme is a glycolate oxidase and the oxidized form of the second electron acceptor is $O_2$, and the glyoxylate converting enzyme is a D-glycerate dehydrogenase and the reduced form of the second electron acceptor is selected from the group consisting of NADH, NADPH, thio-NADH, thio-NADPH, acetyl-NADH, and acetyl-NADPH.

In some embodiments, the glycolate converting enzyme and the glyoxylate converting enzyme in the cycling reaction system of step c) are the same. In some embodiments, both the glycolate converting enzyme and the glyoxylate converting enzyme are a glycolate reductase or a glyoxylate reductase, and wherein the oxidized form of the second electron acceptor is selected from the group consisting of $NAD^+$, $NADP^+$, thio-$NAD^+$, thio-$NADP^+$, acetyl-$NAD^+$, and acetyl-$NADP^+$, and the reduced form of the third electron acceptor is selected from the group consisting of NADH, NADPH, thio-NADH, thio-NADPH, acetyl-NADH, and acetyl-NADPH.

The kits of the invention may further comprise an instruction for carrying out any of the methods described herein, and/or indicating use for prognosis and/or diagnosis of a disease including, but not limited to, atherosclerosis, stroke, multiple sclerosis, Alzheimer's disease, lung cancer, leukemia, and infection.

DETAILED DESCRIPTION OF THE INVENTION

The present invention provides a method for assaying myeloperoxidase activity. In the assay, a sample containing myeloperoxidase or suspected of containing myeloperoxidase is contacted with substrate including serine, hydrogen peroxide, and a halide. If myeloperoxidase is present in the sample, serine is converted into glycolaldehyde, which is further converted into glycolate by a glycoaldehyde converting enzyme. The method then utilizes a cycling reaction system between glycolate and glyoxylate to generate a detectable signal that corresponds to the myeloperoxidase activity.

For clarity of disclosure, and not by way of limitation, the detailed description of the invention is divided into the subsections that follow.

A. Definitions

Unless defined otherwise, all technical and scientific terms used herein have the same meaning as is commonly understood by one of ordinary skill in the art to which this invention belongs. All patents, applications, published applications and other publications referred to herein are incorporated by reference in their entirety. If a definition set forth in this section is contrary to or otherwise inconsistent with a definition set forth in the patents, applications, published applications and other publications that are herein incorporated by reference, the definition set forth in this section prevails over the definition that is incorporated herein by reference.

As used herein, "a" or "an" means "at least one" or "one or more."

As used herein, "myeloperoxidase" (EC 1.11.1.7) refers to an enzyme that catalyzes formation of an oxidized donor and $H_2O$ from the donor and $H_2O_2$. For example, myeloperoxidase catalyzes formation of HOCl and $H_2O$ from $Cl^-$ and $H_2O_2$. It is intended to encompass derivatives, variants, and analogs of myeloperoxidase that do not substantially alter its activity. Myeloperoxidase can be obtained from any sources, such as human, mouse, bovine, rat, fruit fly, etc.

As used herein, "glycoaldehyde converting enzyme" refers to an enzyme which catalyzes formation of glycolate from glycoaldehyde in the presence of an electron acceptor in its oxidized form. It is intended to encompass derivatives, variants, and analogs of glycolaldehyde converting enzyme that do not substantially alter its activity.

As used herein, "glycolate converting enzyme" refers to an enzyme which catalyzes formation of glyoxylate from glycolate in the presence of an electron acceptor in its oxidized form. It is intended to encompass derivatives, variants, and analogs of glycolate converting enzyme that do not substantially alter its activity.

As used herein, "glyoxylate converting enzyme" refers to an enzyme which catalyzes formation of glycolate from glyoxylate in the presence of an electron acceptor in its reduced form. It is intended to encompass derivatives, variants, and analogs of glyoxylate converting enzyme that do not substantially alter its activity.

As used herein the term "assessing" is intended to include quantitative and qualitative determination in the sense of obtaining an absolute value for the amount or concentration of the analyte present in the reaction system, and also of obtaining an index, ratio, percentage, visual or other value indicative of the level of analyte in the reaction system. Assessment may be direct or indirect and the chemical species actually detected need not of course be the analyte itself but may for example be a derivative thereof or some further substance.

As used herein, "sample" refers to anything which may contain an analyte for which an analyte assay is desired. The sample may be a biological sample, such as a biological fluid or a biological tissue. Examples of biological fluids include urine, blood, plasma, serum, saliva, semen, stool, sputum, cerebral spinal fluid, tears, mucus, amniotic fluid or the like. Biological tissues are aggregates of cells, usually of a particular kind together with their intercellular substance that form one of the structural materials of a human, animal, plant, bacterial, fungal or viral structure, including connective, epithelium, muscle and nerve tissues. Examples of biological tissues also include organs, tumors, lymph nodes, arteries and individual cell(s).

As used herein, "serum" refers to the fluid portion of the blood obtained after removal of the fibrin clot and blood cells, distinguished from the plasma in circulating blood.

As used herein, "plasma" refers to the fluid, noncellular portion of the blood, distinguished from the serum obtained after coagulation.

As used herein, "fluid" refers to any composition that can flow. Fluids thus encompass compositions that are in the form of semi-solids, pastes, solutions, aqueous mixtures, gels, lotions, creams and other such compositions.

As used herein, "disease or disorder" refers to a pathological condition in an organism resulting from, e.g., infection or genetic defect, and characterized by identifiable symptoms.

As used herein, "contacting" means bringing two or more components together. "Contacting" can be achieved by mixing all the components in a fluid or semi-fluid mixture. "Contacting" can also be achieved when one or more components are brought into contact with one or more other components on a solid surface such as a solid tissue section or a substrate.

As used herein, a "cycling reaction system" refers to the process of converting glycolate to glyoxylate and from glyoxylate back to glycolate.

B. Methods for Assaying Myeloperoxidase

The invention provides a method for assaying the presence, absence and/or amount of a myeloperoxidase in a sample, said method comprises: a) contacting a sample containing or suspected of containing a myeloperoxidase with serine, hydrogen peroxide, and a halide (preferably chlorine) to generate glycolaldehyde; b) converting said glycolaldehyde generated in step a) to glycolate in the presence of a glycolaldehyde converting enzyme and a first electron acceptor in its oxidized form; c) converting said glycolate from step b) to glyoxylate in the presence of a second electron acceptor in its oxidized form and a glycolate converting enzyme, whereby reduced form of the second electron acceptor is generated; said glyoxylate is converted back to glycolate in the presence of a third electron acceptor in its reduced form and a glyoxylate converting enzyme to form a cycling reaction system, whereby oxidized form of the third electron acceptor is generated; wherein the second electron acceptor and the third electron acceptor are different; and d) assessing at least one detectable signals generated in step c). In some embodiments, the detectable signal generated in step c) is a concentration change of the reduced or oxidized form of the second electron acceptor or the reduced or oxidized form of the third electron acceptor in said cycling reaction system.

Step a): Converting Serine to Glycoaldehyde in the Presence of Hydrogen Peroxide and a Halide by a Myeloperoxidase The methods for assaying myeloperoxidase in the present invention are based on measuring an enzymatic activity catalyzed myeloperoxidases. Myeloperoxidases catalyze reactions which convert serine to glycolaldehyde in the presence of hydrogen peroxide and a halide. Accordingly, the presence or absence and the amount of a myeloperoxidase in a sample can be determined by determining the glycoaldehyde generated in these reactions. The halide in these reactions may be $Cl^-$, $Br^-$, or $I^-$. Preferably, the halide is $Cl^-$. Thus, an exemplary reaction scheme for step a) of the present invention is:

$$\text{Serine}+H_2O_2+Cl^-+H^+\rightarrow\text{glycolaldehyde}+HOCl+H_2O \quad (1)$$

The serine, hydrogen peroxide, and chlorine (or other halides) in step a) can be of any concentration that is suitable for a myeloperoxidase reaction and depends on the activity of myeloperoxidase in the sample. For example, the concentration of serine is about 0.05 mM to about 100 mM; about 0.1 mM to about 0.5 mM, about 1 mM to about 50 mM, or about 5 mM to about 10 mM; hydrogen peroxide is about 5 uM to about 10 mM, about 10 uM to about 1 mM, or about 50 uM to about 500 uM; chlorine (or other halides) is about 1 mM to 500 mM, about 10 mM to 200 mM, or about 100 mM to about 150 mM. Sodium chloride or other salt may be used as a suitable source for chlorine.

Any sample containing or suspected of containing myeloperoxidase can be assayed using the present invention. In some embodiments, the sample is blood, serum, plasma, or urine. In some embodiments, the sample contains leukocytes, such as neutrophils, eosinophils, lymphocytes, and/or monocytes. In some embodiments, the sample is a tissue sample. In some embodiments, the tissue sample is subject to homogenization to obtain a crude tissue homogenate before the assay is conducted.

In some embodiments, the sample is pre-processed before the assay is carried out. Exemplary processing steps include centrifugation, extraction/washing, cell lysis, freeze/thaw, and sonication. The sample may also be diluted before the assay.

Step b): Converting Glycolaldehyde to Glycolate Catalyzed by a Glycolaldehyde Converting Enzyme Step b) of the present invention converts glycolaldehyde to glycolate in the presence of an electron acceptor in its oxidized form through the action of a glycolaldehyde converting enzyme. Any glycolaldehyde converting enzyme that converts glycoaldehyde to glycolate in the presence of an electron acceptor in its oxidized may be used. In some embodiments, the glycolaldehyde converting enzyme is a glycolaldehyde dehydrogenase. Thus, an exemplary reaction scheme catalyzed by a glycolaldehyde dehydrogenase is:

$$\text{Glycolaldehyde}+NAD^++H_2O\rightarrow\text{glycolate}+NADH+H^+ \quad (2)$$

Any glycolaldehyde dehydrogenase can be used. For example, glycolaldehyde dehydrogenase (EC 1.1.1.21) having the amino acid sequences with the following GenBank Accession Nos. A39763 (*Homo sapiens*), A35452 (bovine), A60603 (rat), A34406 (rabbit), I49484 (mouse), A59021 (pig), C85505 (*E. coli*), A97465 (*Agrobacterium tumefaciens*), S46020 (*S. cerevisiae*), and JQ2253 (bromegrass) can be used.

Any electron acceptor that is compatible with the glycolaldehyde converting enzyme chosen may be used. For example, when glycolaldehyde dehydrogenase is used, the electron acceptor (in oxidized form) may be $NAD^+$, $NADP^+$, thio-$NAD^+$, thio-$NADP^+$, acetyl-$NAD^+$, or acetyl-$NADP^+$.

Step c): Glycolate-Glyoxylate Cycling Reaction System

Step c) of the present invention converts glycolate to glyoxylate in the presence of a second electron acceptor (in its oxidized form) through the action of a glycolate converting enzyme, and then from glyoxylate back to glycolate in the presence of a third electron acceptor (in its reduced form) through the action of a glyoxylate converting enzyme. The second electron acceptor and the third electron acceptor are different electron acceptors. Step c) thus forms a cycling reaction system generating an increase of the second electron acceptor in its reduced form and a reduction of the second electron acceptor in its oxidized form, and an increase of the third electron acceptor in its oxidized form and a reduction of the third electron acceptor in its reduced form. The increase of an electron acceptor in a specific form or the reduction of an electron acceptor in a specific form can be measured. In some embodiments, one electron acceptor in the specific form is accumulated and the accumulation is assessed.

In some embodiments, the glycolate converting enzyme and the glyoxylate converting enzyme are different. In some embodiments, the glycolate converting enzyme does not cross-react with the third electron acceptor or binds to the third electron acceptor with a lower affinity than to the second electron acceptor, and the glyoxylate converting enzyme does not cross-react with the second electron acceptor or binds to the second electron acceptor with a lower affinity than to the third electron acceptor.

Any glycolate converting enzyme that catalyzes formation of glyoxylate from glycolate in the presence of an electron acceptor in its oxidized form can be used.

In some embodiments, the glycolate converting enzyme is a glycolate reductase. For example, any glycolate reductase (EC 1.1.1.79) encoded by nucleotide sequences of the GenBank Accession Nos. NC_000913 (*E. coli*), U00096 (*E. coli*), NC_004722 (*Bacillus cereus*), and AE017002 (*Bacillus cereus*) can be used.

In other embodiments, the glycolate converting enzyme is a glycolate oxidase. For example, glycolate oxidase (EC 1.1.3.15) having the amino acid sequence with the following GenBank Accession Nos. S33322 (rat), NP_105534 (*Mesorhizobium loti*), AE3642 (*Brucella melitensis*), T17471 (*Amycolatopsis orientalis*), S74706 (*Synechocystis* sp), T10242 (cucurbit), T02150 (rice), S75231 (*Synechocystis* sp), and OXSPH (spinach) can be used.

In still other embodiments, the glycolate converting enzyme is a glyoxylate reductase. For example, any glyoxylate reductase (EC 1.1.1.26) having the amino acid sequence with the following GenBank Accession Nos. AB033995 (*thermococcus litoralis*) and AF134895 (human) can be used.

Any glyoxylate converting enzyme that catalyzes formation of glycolate from glyoxylate in the presence of an electron acceptor in its reduced form can be used.

In some embodiments, the glyoxylate converting enzyme is a glycerate dehydrogenase. For example, glycerate dehydrogenase (E.C. 1.1.1.29) having the amino acid sequences with the following GenBank Accession Nos. NP_283114 (*Neisseria meningitidis*), CAB83582(*Neisseria meningitidis*), F82022 (*Neisseria meningitis*), S68165 (*Cucurbita*), S68164 (*Cucurbita*), DEKVG (cucumber) can be used.

In other embodiments, the glyoxylate converting enzyme is a glyoxylate reductase. Glyoxylate reductases are described herein.

In still other embodiments, the glyoxylate converting enzyme is glycolate reductase. Glycolate reductases are described herein.

In some embodiments, the glycolate converting enzyme and the glyoxylate converting enzyme are the same. In one embodiment, both the glycolate converting enzyme and the glyoxylate converting enzyme are glycolate reductase. In other embodiment, both the glycolate converting enzyme and the glyoxylate converting enzyme are glyoxylate reductase. Any glycolate reductase and glyoxylate reductase known in the art and described herein may be used.

The second and third electron acceptors can be any electron acceptors that are compatible with the enzymes chosen for the different steps of the reactions, provided that the second electron acceptor and the third electron acceptor are different.

In some embodiments, the glycolate converting enzyme is glycolate reductase and the second electron acceptor is selected from the group consisting of $NAD^+$, $NADP^+$, thio-$NAD^+$, thio-$NADP^+$, acetyl-$NAD^+$, and acetyl-$NADP^+$, lactate, 2-6-dichloroindophenol, and phenazine methosulfate. In some embodiments, the glycolate converting enzyme is glycolate oxidase and the second electron acceptor is $O_2$. In some embodiments, the glycolate converting enzyme is glyoxylate reductase, and the second electron acceptor is selected from the group consisting of $NAD^+$, $NADP^+$, thio-$NAD^+$, thio-$NADP^+$, acetyl-$NAD^+$, and acetyl-$NADP^+$, lactate, 2-6-dichloroindophenol, and phenazine methosulfate.

In some embodiments, the glyoxylate converting enzyme is glyoxylate reductase, and the third electron acceptor is selected from the group consisting of NADH, NADPH, thio-NADH, thio-NADPH, acetyl-NADH, and acetyl-NADPH. In some embodiments, the glyoxylate converting enzyme is D-glycerate dehydrogenase and the third electron acceptor is selected from the group consisting of NADH, NADPH, thio-NADH, thio-NADPH, acetyl-NADH, and acetyl-NADPH. In some embodiments, the glyoxylate converting enzyme is glycolate reductase and the third electron acceptor is selected from the group consisting of NADH, NADPH, thio-NADH, thio-NADPH, acetyl-NADH, and acetyl-NADPH.

In some embodiments, the glycolate converting enzyme and the glyoxylate converting enzyme may collectively catalyze a cycling reaction between glycolate and the glyoxylate that amplifies signals generated in the assay. The glycolate converting enzyme and the glyoxylate converting enzyme may utilize different electron acceptors and do not cross-react with electron acceptors used by the other enzyme or react with low affinity. Alternatively, the two enzymes may recognize the same electron acceptors. Sufficient amount of oxidized form of the second electron acceptor and reduced form of the third electron acceptor can be added to the cycling reaction to drive both reactions and allow the cycle to go on until sufficient signal is generated.

In the following two exemplary reaction schemes for step c), the glycolate converting enzyme and the glyoxylate converting enzyme are different. For example, the glycolate converting enzyme is glycolate reductase and the glyoxylate converting enzyme is glyoxylate reductase. Thus, an exemplary reaction scheme for step c) is:

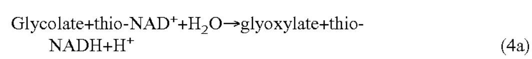

Glycolate+thio-$NAD^+$+$H_2O$→glyoxylate+thio-NADH+$H^+$ (4a)

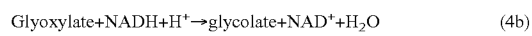

Glyoxylate+NADH+$H^+$→glycolate+$NAD^+$+$H_2O$ (4b)

Reaction (4a) represents a reaction catalyzed by a glycolate reductase, and reaction (4b) represents a reaction catalyzed by a glyoxylate reductase. Sufficient thio-$NAD^+$ and NADH can be added to the reaction to generate a cycling reaction, which leads to accumulation of thio-NADH.

In another example, glycolate oxidase is used as the glycolate converting enzyme, and D-glycerate dehydrogenase is used the glyoxylate converting enzyme in the cycling reaction. An exemplary reaction scheme is:

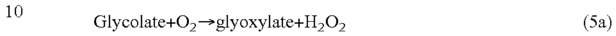

Glycolate+$O_2$→glyoxylate+$H_2O_2$ (5a)

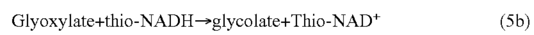

Glyoxylate+thio-NADH→glycolate+Thio-$NAD^+$ (5b)

Reaction (5a) represents a reaction catalyzed by a glycolate oxidase, and reaction (5b) represents a reaction catalyzed by a D-glycerate dehydrogenase. Sufficient amount of $O_2$ and thio-NADH can be added to the reaction to generate a cycling reaction, which leads to accumulation of thio-$NAD^+$ and $H_2O_2$.

The following is an exemplary reaction scheme, in which the glycolate converting enzyme and the glyoxylate converting enzyme are the same. One such exemplary reaction scheme is:

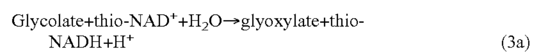

Glycolate+thio-$NAD^+$+$H_2O$→glyoxylate+thio-NADH+$H^+$ (3a)

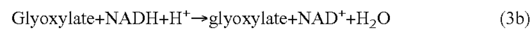

Glyoxylate+NADH+$H^+$→glyoxylate+$NAD^+$+$H_2O$ (3b)

Both reaction (3a) and (3b) are catalyzed by the same enzyme, which is a glycolate reductase or a glyoxylate reductase. Sufficient thio-$NAD^+$ and NADH can be added to the reaction mix to drive both reactions in a cycling reaction that leads to accumulation of thio-NADH.

Any other combinations of glycolate converting enzymes and glyoxylate converting enzymes may be used to achieve the same cycling effect.

The enzymatic reactions in steps a) through c) are generally carried out in a condition (such as buffer and temperature) suitable for the completion of the enzymatic reactions. The buffer used for steps a), b), and c) described herein can be the same or can be different. Any buffer known in the art suitable for the specific enzymatic reaction can be used. For example, the buffer can be a phosphate buffer with a pH of about 6 to about 8; a Tris-HCl buffer with a pH of about 7 to about 9, or a Good's buffer with a pH of about 6 to about 9.

The temperature for each step can be the same or different. The temperature is preferably between about 25 to about 37° C.

In some embodiments, one or more steps described herein are carried out in a separate reaction mixture. For example, the end products of one or more steps in the reaction can be partially or completely separated from the reaction mixture before reagents for the next step are added.

In some embodiments, steps a) through c) described herein are carried out in a single reaction mixture.

In some embodiments, the enzymes, substrates, or electronic acceptors for the next step are added sequentially to the same reaction mix at the end of a previous step. In some embodiments, the reaction in a previous step is terminated before reagents for the next step are added. In some embodiment, some or all reagents for more than one step are added simultaneously to the reaction mixture. In some embodiments, reagents for steps a) and b) are mixed with the sample at the same time. In these embodiments, the sample suspected of containing a myeloperoxidase is contacted with serine, hydrogen peroxide, chlorine, the glycolaldehyde converting enzyme, and the first electron acceptor in its oxidized form. In some embodiments, reagents for steps a), b), and some of the reagents for step c) are mixed with the sample at the same time. In these embodiments, the sample suspected of containing a myeloperoxidase is contacted with serine, hydrogen peroxide, chlorine, the glycolaldehyde converting enzyme, the first electron acceptor in its oxidized form, the glycolate converting enzyme, and the second electron acceptor in its oxidized form. In other embodiments, reagents for steps a), b), and c) are mixed with the sample at the same time. In these embodiments, the sample suspected of containing a myeloperoxidase is contacted with serine, hydrogen peroxide, chlorine, the glycolaldehyde converting enzyme, the first electron acceptor in its oxidized form, the glycolate converting enzyme, the second electron acceptor in its oxidized form, the glyoxylate converting enzyme, and the third electron acceptor in its reduced form.

In some embodiments, the first electron acceptor is different from the second and/or the third electron acceptor. In other embodiments, the first electron acceptor is the same as the second electron acceptor. In still other embodiments, the first electron acceptor is the same as the third electron acceptor.

Step d): Assessing Signals Generated in Step c)

The quantification of myeloperoxidase in the sample can be achieved by monitoring the subtractive or additive difference in the signal generated in step c). The assessment can be carried out continuously or at different time points.

In some embodiments, the concentration change of the reduced or oxidized form of the second electron acceptor is assessed. In some embodiments, the activity of myeloperoxidase is determined by assessing an increase in concentration of the reduced form of the second electron acceptor. In some embodiments, the activity of myeloperoxidase is determined by assessing a decrease in concentration of the oxidized form of the second electron acceptor.

In some embodiments, the concentration change of the reduced or oxidized form of the third electron acceptor is assessed. In some embodiments, the activity of myeloperoxidase is determined by assessing a decrease in concentration of the reduced form of the third electron acceptor. In some embodiments, the activity of myeloperoxidase is determined by assessing an increase in concentration of the oxidized form of the third electron acceptor.

The concentration changes of electron acceptors described herein can be assessed using methods known in the art. For example, the concentration changes of NADH or NADPH can be determined spectrophotometrically by measuring the absorption at 340 nm. The concentration changes of thio-NADH can be determined spectrophotometrically by measuring absorption at 405 nm.

In some embodiments, the concentration changes NADH or NADPH can be measured by colorimetric method using an electron transport chromogens, including, but not limited to, 3-(p-iodophenyl)-2-(p-nitrophenyl)-5-phenyl-2H-tetrazolium chloride, 3-(4,5-dimethyl-2-thiazolyl)-2,5-diphenyl-2H-tetrazolium bromide, 3,3'-(4,4'-biphenylene)-bis(2,5-diphenyl-2H-tetrazolium chloride), 3,3'-(3,3'-dimethoxy-4,4'-biphenylene)-bis[2-(p-nitrophenyl)-5-phenyl-2H-tetrazolium chloride] (=nitro-tetrazolium: NTB), 3,3'-(3,3'-dimethoxy-4,4'biphenylene)-bis[2,5-bis(p-nitrophenyl)-2H-tetraz olium chloride], 3,3'-(3,3'-dimethoxy-4,4'-biphenylene)-bis(2,5-diphenyl-2H-tetrazolium chloride), and 2,6-dichlorophenol-indophenol. A preferred example is a combination of water-soluble tetrazolium salt and diaphorase or phenazinemethosulfate. These electron transport chromogens are electron acceptors for NADP or NADPH to form a colored formazane pigment, and the formed pigment is calorimetrically measured at the maximum absorption thereof.

A further assay method for NADH or NADPH is fluorometry wherein NAD or NADPH is treated with diaphorase in the presence of a fluorescent reagent such as resazulin.

Measurement of concentration of reduced and/or oxidized forms of electron acceptors described herein are known in the art. For example, the amount of consumed $O_2$ or $H_2O_2$ formed can be assayed by the use of electronic sensors. Numerous red-ox indicators can be used for this purpose, and a wide range of methods are described in the literature for assaying $H_2O_2$ and $O_2$ in solution. Generated $H_2O_2$ can also be measured as a detectable product by reacting with an indicator and $H_2O_2$. Examples of indicators are reagents which can be measured by spectrophotometric means, color indicators, fluorescent reagents or luminescent reagents. For example, $H_2O_2$ can be assessed using the non-enzymatic chemiluminescent reactions of peroxioxalate and the acridinium esters.

Assays may be performed in duplicates with both positive and background controls. A standard curve can be obtained by using known amounts of myeloperoxidase with known activity. The levels of myeloperoxidase in each sample can then be determined by comparing each signal measured to the standard curve.

C. Uses of the Methods

The present invention provides an assay with increased sensitivity for detecting even small amounts of myeloperoxidase present in a sample. The methods of the invention thus provides a practical means for detecting conditions associated with altered levels of myeloperoxidase and monitoring myeloperoxidase levels in a patient. The method can be used for prognosis or diagnosis of any disease associated with an inappropriate amount or reaction to myeloperoxidase present, or the effect or activity of such, in a subject. Examples of such diseases include, but are not limited to, acute myeloid leukemia, systemic lupus erythrematosas, Hashimoto's thyroidiris, myasthenia gravis, rheumatoid arthritis, multiple sclerosis, Guillan Barre syndrome, glomerulonephritis, atherosclerosis, stroke, multiple sclerosis, Alzheimer's disease, leukemia, infection, asthma, cancer such as lung cancer, cystic fibrosis, chronic obstructive pulmonary disease, inflammatory bowel disease, and neuroinflammatory diseases.

The enzymatic assay of the present invention also provides a research tool for the exploration of the role of myeloperoxidase in biological processes and various pathological conditions.

D. Kits for Assaying Myeloperoxidase

The present invention also provides kits for assaying myeloperoxidase activities, such as a diagnostic kit. Such kits comprise one or more substrates, enzymatic agents and electron acceptors described herein for carrying out the methods of the present invention, e.g., serine, hydrogen peroxide, chlorine (or other halides), glycolaldehyde converting enzyme, first electron acceptor in its oxidized form, glycolate converting enzyme, second electron acceptor in its oxidized form, glyoxylate converting enzyme, third electron acceptor in its reduced form, wherein the second electron acceptor and the third electron acceptor are different. Any of the substrates, enzymes, and electron acceptors described herein may be included in the kit. The kits may also comprise positive and/or negative control standards, as well as necessary reagents for assessing the signals generated by step c), for example, reagents for conducting a colormetic assay may be included. The kits may also comprise an apparatus or container for conducting the methods of the invention and/or transferring samples to a diagnostic laboratory for processing, as well as suitable instructions for carrying out the methods of the invention.

The kits of the invention may be in any suitable packaging. For example, the packages discussed herein in relation to diagnostic systems are those customarily utilized in diagnostic systems. Such packages include containers appropriate for use in autoanalyzers.

E. EXAMPLES

The following examples are included for illustrative purposes only and are not intend to limit the scope o the invention.

Example 1

Myeloperoxidase Assay Using Glycolate Reductase and Glyoxylate Reductase

In this study, the glycolaldehyde converting enzyme is glycolaldehyde dehydrogenase, the glycolate converting enzyme is glycolate reductase, and the glyoxylate converting enzyme is glyoxylate reductase. The reagents used in this study are set forth in the following Tables 1 and 2.

TABLE 1

Compositions of Reagent 1

| Chemical Reagents | Concentration |
|---|---|
| Potassium phosphate, pH 6.0 | 25 mM |
| NaCl | 150 mM |
| L-Serine | 200 uM |
| $H_2O_2$ | 200 uM |
| Thio-$NAD^+$ | 0.3 mM |
| Glycolaldehyde dehydrogenase | 20 U/ml |

TABLE 2

Compositions of Reagent 2

| Chemical Reagents | Concentration |
|---|---|
| Potassium phosphate, pH 8.0 | 100 mM |
| Glycolate reductase | 50 U/ml |
| NADH | 0.6 mM |
| Glyoxylate reductase | 15 U/ml |

In this study, 250 ul of Reagent 1 is mixed with 20 ul of sample to be tested and the mixture is incubated at 37° C. for five minutes. 50 ul of Reagent 2 is then added to the mixture and incubated at 37° C. for another one minute. After the incubation, the change of the absorbance at 405 nm is measured continuously for 2 minutes.

Example 2

Myeloperoxidase Assay Using Glycolate Oxidase and D-Glycerate Dehydrogenase

In this study, the glycolaldehyde converting enzyme is glycolaldehyde dehydrogenase, the glycolate converting enzyme is glycolate oxidase, and the glyoxylate converting enzyme is D-glycerate dehydrogenase. The reagents used in this study are set forth in the following Tables 3 and 4.

TABLE 3

Compositions of Reagent 1

| Chemical Reagents | Concentration |
|---|---|
| Potassium phosphate, pH 6.0 | 25 mM |
| NaCl | 150 mM |
| L-Serine | 500 uM |
| $H_2O_2$ | 200 uM |
| $NAD^+$ | 0.3 mM |
| Glycolaldehyde dehydrogenase | 50 U/ml |
| Glycolate oxidase | 30 U/ml |

TABLE 4

Compositions of Reagent 2

| Chemical Reagents | Concentration |
|---|---|
| Potassium phosphate, pH 8.5 | 100 mM |
| Thio-NADH | 0.8 mM |
| D-glycerate dehydrogenase | 15 U/ml |

In this study, 280 ul of Reagent 1 is mixed with 30 ul of sample to be tested and the mixture is incubated at 37 C for five minutes. 60 ul of Reagent 2 is then added to the mixture and is incubated at 37 C for another two minutes. After the incubation, the change of the absorbance at 405 nm is measured continuously for 2 minutes.

Example 3

Myeloperoxidase Assay Using Glycolate Reductase

In this study, the glycolaldehyde converting enzyme is glycolaldehyde dehydrogenase, the glycolate converting enzyme and the glyoxylate converting enzyme are both glycolate reductase. The reagents used in this study are set forth in the following Tables 5 and 6.

TABLE 5

Compositions of Reagent 1

| Chemical Reagents | Concentration |
|---|---|
| Good's buffer, pH 6.0 | 25 mM |
| NaCl | 200 mM |
| L-Serine | 300 uM |
| $H_2O_2$ | 250 uM |
| $NAD^+$ | 0.3 mM |
| Glycolaldehyde dehydrogenase | 10 U/ml |

TABLE 6

Compositions of Reagent 2

| Chemical Reagents | Concentration |
|---|---|
| Tris-HCl, pH 7.0 | 100 mM |
| Thio-$NAD^+$ | 1.2 mM |
| NADH | 0.8 mM |
| Glycolate reductase | 40 U/ml |

In this study, 240 ul of Reagent 1 is mixed with 20 ul of sample to be tested and the mixture is incubated at 37° C. for five minutes. 60 ul of reagent 2 is then added to the mixture and is incubated at 37° C. for another one minute. After the incubation, the change of the absorbance at 405 nm is measured continuously for 2 minutes.

The above examples are included for illustrative purposes only and are not intended to limit the scope of the invention. Many variations to those described above are possible. Since modifications and variations to the examples described above will be apparent to those of skill in this art, it is intended that this invention be limited only by the scope of the appended claims.

The claimed invention is:

1. A method for assaying a myeloperoxidase in a sample, said method comprises:

a) contacting a sample suspected of containing a myeloperoxidase with serine, hydrogen peroxide, and chlorine to generate glycolaldehyde;

b) converting said glycolaldehyde generated in step a) to glycolate in the presence of a glycolaldehyde converting enzyme and a first electron acceptor in its oxidized form;

c) converting said glycolate from step b) to glyoxylate in the presence of a second electron acceptor in its oxidized form and a glycolate converting enzyme, whereby reduced form of the second electron acceptor is generated; said glyoxylate is converted back to glycolate in the presence of a third electron acceptor in its reduced form and a glyoxylate converting enzyme to form a cycling reaction system, whereby oxidized form of the third electron acceptor is generated; wherein the second electron acceptor and the third electron acceptor are different; and d) assessing concentration change of the reduced or oxidized form of the second electron acceptor or the reduced or oxidized form of the third electron acceptor in said cycling reaction system, whereby the presence, absence and/or the amount of the myeloperoxidase in the sample is determined.

2. The method of claim 1, wherein the first electron acceptor and the second electron acceptor are the same.

3. The method of claim 1, wherein the sample suspected of containing a myeloperoxidase is contacted with serine, hydrogen peroxide, chlorine, the glycolaldehyde converting enzyme, and the first electron acceptor in its oxidized form, wherein these reagents are all mixed with the sample at the same time.

4. The method of claim 1, wherein the sample suspected of containing a myeloperoxidase is contacted with serine, hydrogen peroxide, chlorine, the glycolaldehyde converting enzyme, the first electron acceptor in its oxidized form, the glycolate converting enzyme, and the second electron acceptor in its oxidized form, wherein the reagents are all mixed with the sample at the same time.

5. The method of claim 1, wherein the glycolaldehyde converting enzyme of step b) is a glycolaldehyde dehydrogenase, and the first electron acceptor is selected from the group consisting of $NAD^+$, $NADP^+$, thio-$NAD^+$, thio-$NADP^+$, acetyl-$NAD^+$, and acetyl-$NADP^+$.

6. The method of claim 1, wherein the glycolate converting enzyme and the glyoxylate converting enzyme in the cycling reaction system of step c) are different.

7. The method of claim 6, wherein the glycolate converting enzyme is a glycolate reductase or a glycolate oxidase.

8. The method of claim 6, wherein the glyoxylate converting enzyme is a glyoxylate reductase or a D-glycerate dehydrogenase.

9. The method of claim 6, wherein the glycolate converting enzyme is a glycolate reductase, and the glyoxylate converting enzyme is a glyoxylate reductase.

10. The method of claim 9, wherein the oxidized form of the second electron acceptor is selected from the group consisting of $NAD^+$, $NADP^+$, thio-$NAD^+$, thio-$NADP^+$, acetyl-$NAD^+$, and acetyl-$NADP^+$, and the reduced form of the third electron acceptor is selected from the group consisting of NADH, NADPH, thio-NADH, thio-NADPH, acetyl-NADH, acetyl-NADPH, (R)-lactate, 2,6-dichloroindophenol, and phenazine methosulfate.

11. The method of claim 6, wherein the glycolate converting enzyme is a glycolate oxidase, and the glyoxylate converting enzyme is a D-glycerate dehydrogenase.

12. The method of claim 11, wherein the oxidized form of the second electron acceptor is $O_2$, and the reduced form of the third electron acceptor is selected from the group consisting of NADH, NADPH, thio-NADH, thio-NADPH, acetyl-NADH, acetyl-NADPH.

13. The method of claim 1, wherein the glycolate converting enzyme and the glyoxylate converting enzyme in the cycling reaction system of step c) are the same.

14. The method of claim 13, wherein both the glycolate converting enzyme and the glyoxylate converting enzyme are a glycolate reductase or a glyoxylate reductase.

15. The method of claim 14, wherein the oxidized form of the second electron acceptor is selected from the group consisting of $NAD^+$, $NADP^+$, thio-$NAD^+$, thio-$NADP^+$, acetyl-$NAD^+$, and acetyl-$NADP^+$, and the reduced form of the third electron acceptor is selected from a group consisting of NADH, NADPH, thio-NADH, thio-NADPH, acetyl-NADH, and acetyl-NADPH.

16. The method of claim 1, wherein the concentration change is assessed by photometric method.

17. The method of claim 1, said method further comprises a step of coupling the oxidized or reduced form of the second electron acceptor or the reduced or oxidized form of the third electron acceptor to a color-producing agent after step d), wherein the concentration change of the oxidized or reduced form of the second electron acceptor or the reduced or oxidized form of the third electron acceptor is assessed by a colorimetric method.

18. The method of claim 1, wherein the sample is a biological fluid.

19. The method of claim 18, wherein the biological fluid is selected from the group consisting of blood, serum, plasma and urine.

20. The method of claim 1, said method is used for prognosis and/or diagnosis of a disease.

21. The method of claim 20, wherein the disease is selected from the group consisting of atherosclerosis, stroke, multiple sclerosis, Alzheimer's disease, lung cancer, leukemia, and infection.

* * * * *